(12) United States Patent
Gaitonde et al.

(10) Patent No.: US 8,785,461 B2
(45) Date of Patent: Jul. 22, 2014

(54) PROCESS FOR PREPARING BOSENTAN

(75) Inventors: Abhay Gaitonde, Maharashtra (IN);
Bindu Manojkumar, Maharashtra (IN);
Sandeep Mekde, Maharashtra (IN);
Vikas Padalkar, Maharashtra (IN);
Hemant Mande, Maharashtra (IN)

(73) Assignee: Generics [UK] Limited, Hertfordshire (GB)

( * ) Notice: Subject to any disclaimer, the term of this patent is extended or adjusted under 35 U.S.C. 154(b) by 125 days.

(21) Appl. No.: 12/866,373

(22) PCT Filed: Feb. 6, 2009

(86) PCT No.: PCT/GB2009/050120
§ 371 (c)(1),
(2), (4) Date: Oct. 29, 2010

(87) PCT Pub. No.: WO2009/098517
PCT Pub. Date: Aug. 13, 2009

(65) Prior Publication Data
US 2011/0039871 A1    Feb. 17, 2011

(30) Foreign Application Priority Data
Feb. 8, 2008 (IN) .............................. 228/KOL/2008

(51) Int. Cl.
*A01N 43/54* (2006.01)
*A61K 31/505* (2006.01)

(52) U.S. Cl.
USPC .......................................... 514/269; 544/296

(58) Field of Classification Search
USPC .......................................... 544/296; 514/269
See application file for complete search history.

(56) References Cited

U.S. PATENT DOCUMENTS

| | | | |
|---|---|---|---|
| 5,292,740 A * | 3/1994 | Burri et al. | 514/256 |
| 5,739,333 A * | 4/1998 | Yamada et al. | 544/296 |
| 6,136,971 A * | 10/2000 | Harrington et al. | 544/122 |
| 6,479,692 B1 | 11/2002 | Ekwuribe et al. | |
| 8,288,401 B2 | 10/2012 | Gaitonde et al. | |
| 2008/0188663 A1 | 8/2008 | Kumar et al. | |
| 2008/0242687 A1 | 10/2008 | Gant et al. | |
| 2009/0156811 A1* | 6/2009 | Taddei et al. | 544/296 |
| 2009/0291974 A1* | 11/2009 | Zhu | 514/269 |
| 2010/0261742 A1 | 10/2010 | Gaitonde et al. | |
| 2010/0331352 A1 | 12/2010 | Gaitonde et al. | |
| 2011/0014291 A1 | 1/2011 | Dixit et al. | |
| 2012/0041200 A1 | 2/2012 | Biffi et al. | |

FOREIGN PATENT DOCUMENTS

| | | |
|---|---|---|
| CA | 2 071 193 | 5/1992 |
| CA | 2646795 | 6/2009 |
| CN | 1 425 007 | 6/2003 |
| CN | 101175484 A | 5/2008 |
| EP | 0 526 708 | 2/1993 |
| EP | 0 526 708 B1 | 2/1993 |
| EP | 0 743 307 | 11/1996 |
| EP | 0 743 307 B1 | 9/2001 |
| EP | 2 072 503 | 6/2009 |
| IN | 1245/MUM/2007 | 6/2007 |
| WO | WO 01/36384 | 5/2001 |
| WO | WO 01/43742 | 6/2001 |
| WO | WO 0155120 A1 * | 8/2001 |
| WO | WO 2004/076443 | 9/2004 |
| WO | WO 2004/081016 | 9/2004 |
| WO | WO 2004/087660 | 10/2004 |
| WO | WO 2006123285 A2 | 11/2006 |
| WO | WO 2008/135795 | 11/2008 |
| WO | WO 2009/004374 | 1/2009 |
| WO | WO 2009/047637 | 4/2009 |
| WO | WO 2009/053748 | 4/2009 |
| WO | WO 2009/093127 | 7/2009 |
| WO | WO 2009/095933 | 8/2009 |
| WO | WO 2009/112954 | 9/2009 |
| WO | WO 2010/061210 | 6/2010 |

OTHER PUBLICATIONS

J.H. Poupaert, Drug Design: Basic Principles and Applications, in 2 Encyclopedia of Pharmaceutical Technology 1362-1369, 1367 (James Swarbrick ed., 3rd ed., 2007).*
C. Boss et al., Bioorganic & Medicinal Chemistry Letters, 13, 951-954 (2003).*
International Preliminary Report on Patentability for International Application No. PCT/GB2009/050120 mailed Aug. 19, 2010.
Written Opinion for International Application No. PCT/GB2009/050120 mailed Aug. 19, 2010.
Background Information for the Oct. 2002 ACPS Meeting. Scientific Considerations of Polymorphism in Pharmaceutical Solids: Abbreviated New Drug Applications.
Bioorganic & Medicinal Chemistry, vol. 9, 2001, pp. 2955-2968.
Bosentan Wikipedia extract 26.6.08.
Chemblink webpage re 4,6-dichloro-5-(2-methoxyphenoxy)-2,2'-bipyrimidine 19.1.09.
Chemburkar et al., Organic Process Research & Development, vol. 4, 2000, pp. 413-417.
Chinese Journal of Medicinal Chemistry, vol. 15, 2005, pp. 230-233.
Chromatographia, 2002, vol. 55. pp. S115-S119.
Comprehensive Heterocyclic Chemistry, vol. 3, 1984, pp. 98-101 and 134.
Dunitz et al., Acc. Chem. Res., vol. 28, 1995, pp. 193-200.
EMEA 2005.
Heterocyclic Compounds—The Pyrimidines, 1994, XP-002495603, pp. 397-401.

(Continued)

*Primary Examiner* — Deepak Rao
*Assistant Examiner* — Alexander R Pagano
(74) *Attorney, Agent, or Firm* — Fulbright & Jaworski LLP; Scott D. Rothenberger

(57) ABSTRACT

The present invention relates to a novel intermediate useful in the preparation of bosentan and to processes for the preparation of said intermediate and bosentan. The invention further relates to compositions comprising bosentan prepared according to the processes of the invention and their use in the treatment of endothelin-receptor mediated disorders.

18 Claims, No Drawings

(56) References Cited

OTHER PUBLICATIONS

J.K. Guillory, Generation of Polymorphs, Hydrates, Solvates and Amorphous Solids, in Polymorphism in Pharmaceutical Solids, pp. 183-226 (H.G. Brittain ed. 1999).
J. Lang, Application Note, Thermal Analysis, Perkin Elmer, 2010.
Journal of Chromatography A, 1995, vol. 712(1), pp. 75-83.
Journal of the American Society for Mass Spectrometry, 1999, vol. 10(12), pp. 1305-1314.
Journal of Mass Spectrometry, 1996, vol. 31, pp. 69-76.
Journal of Chromatography B, 2000, vol. 749(1), pp. 67-83.
Martinez-Oharriz et al., Journal of Pharmaceutical Sciences, 1994, vol. 83(2), pp. 174-177.
Modern Drug Discovery, Mar. 2000, p. 53, K. Knapman.
Neidhard W. et al., Chimia, vol. 50, 1996, pp. 519-524.
Organic Process Research and Development, vol. 6, 2002, pp. 120-124.
"Protection of a reactive group" IUPAC Gold Book 2011.
S.L. Morisette et al., Advanced Drug Delivery Reviews, vol. 56, 2004, pp. 275-300.
S.R. Vippagunta et al., Advanced Drug Delivery Reviews, vol. 48, 2001, pp. 3-26.
Swanepoel et al., European Journal of Pharmaceuticals and Biopharmaceutics, 2003, vol. 55, pp. 345-349.
Topics in Current Chemistry, vol. 198, 1998, pp. 163-208.
T.W. Greeene & P.G.M. Wuts, Protective Groups in Organic Synthesis (3rd Ed., John Wily & Sons, 1999) re hydroxyl protection.
Uses of X-ray Powder Diffraction in the Pharmaceutical Industry; in Pharmaceutical Sciences Encyclopedia: Drug Discovery, Development, and Manufacturing, Edited by Shayne C. Gad, John Wiley & Sons, 2010.
Wu et al., Journal of Pharmaceutical Sciences, 1994, vol. 83(10), pp. 1404-1406.
Joel Bernstein, Table 4.6, Polymorphism in Molecular Crystals, Clarendon Press, Oxford, 2002, 3 pages.
Metabolite Services at JIC, Mar. 8, 2009, 2 pages, www.jic.ac.uk/services/metabolomics/topics/lcms/why.htm.
Newport Premium Report, Bosentan monohydrate, downloaded Sep. 4, 2013, 2 pages.

* cited by examiner

PROCESS FOR PREPARING BOSENTAN

CROSS-REFERENCE TO RELATED APPLICATIONS

This application is the U.S. National Stage application of International Application No. PCT/GB2009/050120, filed Feb. 6, 2009, which claims priority to 228/KOL/2008, filed Feb. 8, 2008, the disclosure of which is hereby incorporated by reference.

FIELD OF THE INVENTION

The present invention relates to a novel intermediate useful in the preparation of bosentan and to processes for the preparation of said intermediate and bosentan. The invention further relates to compositions comprising bosentan prepared according to the processes of the invention and their use in the treatment of endothelin-receptor mediated disorders.

BACKGROUND OF THE INVENTION

Bosentan, represented by structural formula (i) and chemically named 4-tert-butyl-N-[6-(2-hydroxyethoxy)-5-(2-methoxyphenoxy)-2-(2-pyrimidinyl)-pyrimidin-4-yl]-benzene-sulfonamide is an endothelin receptor antagonist. It is used for the treatment of disorders which are associated with endothelin activities, in particular circulatory and cardiovascular disorders such as hypertension, ischemia, pulmonary hypertension, vasospasm and angina pectoris. The marketed product comprising bosentan, Tracleer®, is indicated for the treatment of pulmonary arterial hypertension (PAH) to improve exercise capacity and symptoms in patients with grade III functional status.

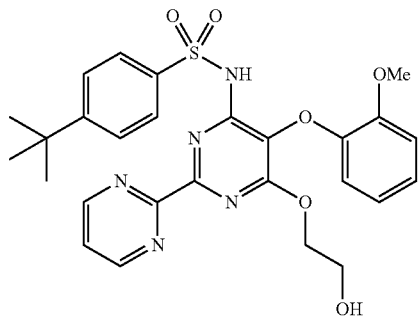

(i)

Bosentan was first described in U.S. Pat. No. 5,292,740. The preparation method involves two steps (as shown in Scheme 1) starting from the dichloro compound, 4,6-dichloro-5-(o-methoxyphenoxy)-2,2'-bipyrimidine (1). The second reaction step is carried out in ethylene glycol with sodium metal used as the base at a temperature of 100-110° C.

Scheme 1

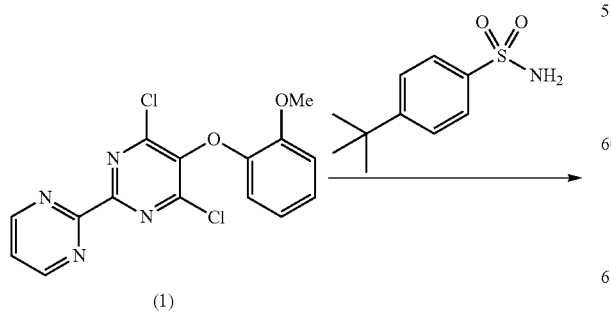

(1)

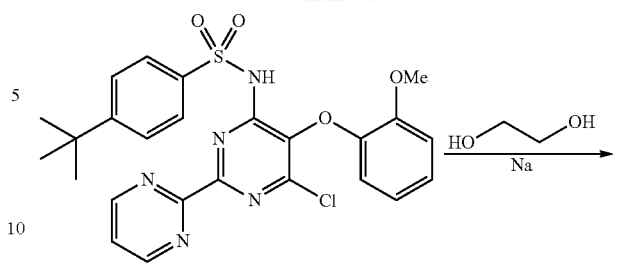

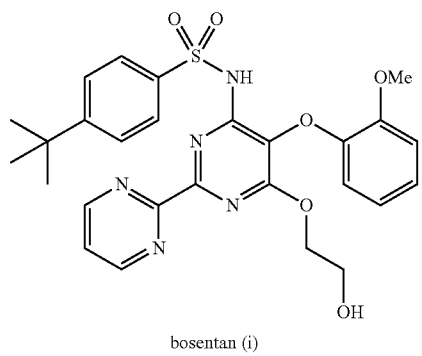

bosentan (i)

One of the disadvantages of this process is the formation of an undesired ethylene glycol bis-sulfonamide dimer having formula (ii) in which two molecules of the pyrimidine monohalide molecule are coupled with one molecule of ethylene glycol. The removal of this impurity requires costly and laborious separation steps. To minimize the formation of this impurity a large excess of ethylene glycol is used. However, using a large excess of ethylene glycol is impractical on a large industrial scale, because ethylene glycol is toxic and its high boiling point means that its removal by distillation is energy and time consuming.

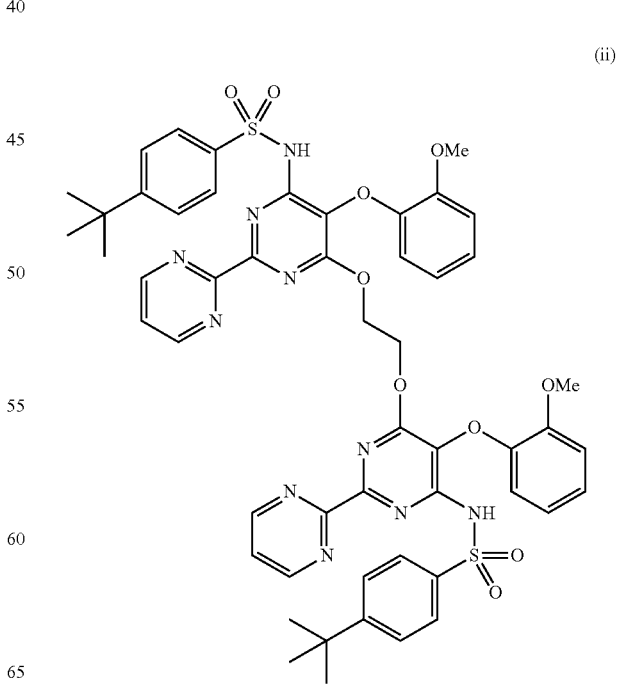

(ii)

Many other processes have been disclosed for the preparation of bosentan, however, they are all multistep processes requiring cumbersome purification processes to obtain the pure product.

U.S. Pat. No. 6,136,971 discloses a process (as shown in Scheme 2) for the preparation of bosentan with high HPLC purity (99.1%) and solves the problem of the dimer formation by utilising a mono-protected 1,2-diheteroethylene anion. In a particularly preferred aspect of the disclosed invention the protecting group is a tert-butyl group used to protect one hydroxyl group of ethylene glycol as an ether. The protecting group is then removed with formic acid to produce a formyloxy-protected ethylene glycol sulfonamide derivative. Treatment of this compound with a base, preferably sodium hydroxide, then produces an ethylene glycol sulfonamide derivative containing a free hydroxy group, namely bosentan.

Scheme 2

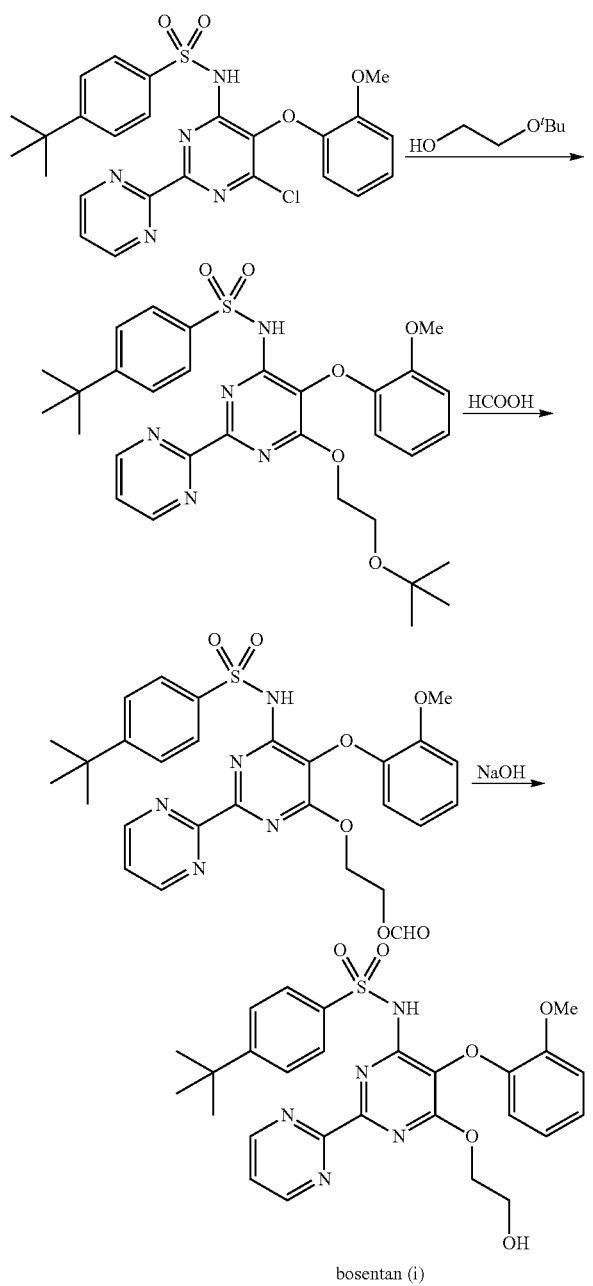

In view of the above disadvantages associated with the prior art there is a need for an improved process for the preparation of bosentan which is economical and high yielding and which provides bosentan with a high degree of purity.

SUMMARY OF THE INVENTION

The present inventors have found that coupling of a dichloro compound, 4,6-dichloro-5-(2-methoxyphenoxy)-2, 2'-bipyrimidine (1), with a mono-protected ethylene glycol of formula HOCH$_2$CH$_2$OR, wherein R is a hydroxyl protecting moiety, followed by introduction of a sulfonamide group in the next step provides an improved process for the preparation of bosentan with a very high purity. This process has the unique and surprising advantage of requiring less sulfonamide than prior art processes, which is an expensive raw material compared to the ethylene glycol derivative.

DETAILED DESCRIPTION OF THE INVENTION

The present invention provides an efficient and economical synthesis of bosentan, which is high yielding and affords the product with very high purity on a commercial scale.

The present inventors have found that coupling the dichloro compound (1) with the mono-protected ethylene glycol component first and then introducing the sulfonamide moiety in a second step as opposed to the prior art processes where the sulfonamide moiety is coupled to the dichloro compound (1) first and the mono-protected ethylene glycol is added in a second step, provides a process with a number of surprising advantages. In particular the process, which further provides a novel intermediate having formula (2a) according to the invention, results in bosentan having a purity of more than 99.70%, preferably greater than 99.8%, and most preferably more than 99.9%. Such purity levels have not been seen before in the prior art.

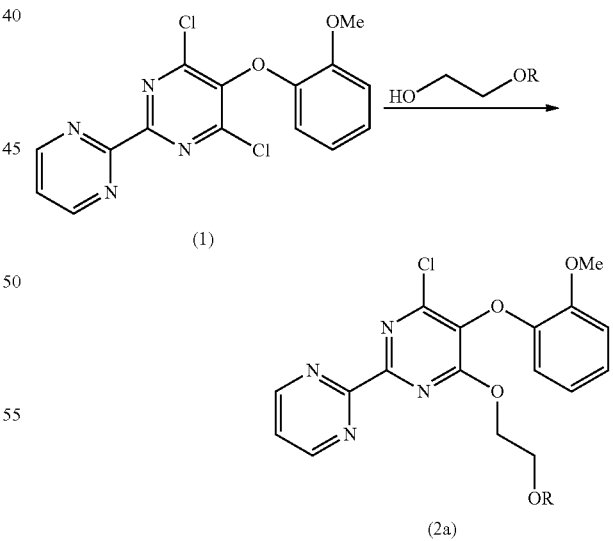

Accordingly, a first aspect according to the invention provides an improved process for the preparation of bosentan utilizing a compound of formula (2a). In one embodiment according to the invention the process comprises the steps of: (a) adding a dichloro compound of formula (1) to a mono-protected ethylene glycol of formula HOCH$_2$CH$_2$OR, wherein R is a hydroxyl protecting moiety, resulting in a reaction mixture comprising a compound of formula (2a);
(b) coupling compound (2a) with 4-tert-butyl phenyl sulfonamide;
(c) removing the protecting moiety R; and
(d) isolating bosentan from the mixture obtained in step (c).

In a particularly preferred embodiment R is stable in basic and mildly acidic conditions. Of course the skilled person will realize that there are a number of further groups that may serve as protecting moieties on the ethylene glycol, indeed any hydroxyl protecting groups that are stable under basic and mildly acidic conditions will be suitable for use in the working of the invention. Examples of said protecting groups can be found in T.W. Greene & P.G.M. Wuts, Protective Groups in Organic Synthesis (3$^{rd}$ ed., John Wiley & Sons, 1999), which is incorporated herein by reference. Accordingly, particularly preferred R groups may be selected from the group comprising alkyl, aryl, arylalkyl, allyl, silyl, benzoate and pivalate moieties. In a particularly preferred embodiment R is tert-butyl.

A preferred reaction temperature for this coupling of the mono-protected ethylene glycol and the 4,6-dichloro-5-(2-methoxyphenoxy)-2,2'-bipyrimidine (1) is from about 15° C. to about 90° C., more preferably from about 30° C. to about 90° C., and most preferably form about 50° C. to about 60° C. A preferred reaction time is about 1-10 hours, more preferably about 1-5 hours, and most preferably about 1-3 hours. Preferably from about 1 equivalents (eq) to about 10 equivalents (eq) of mono-protected ethylene glycol relative to 4,6-dichloro-5-(2-methoxyphenoxy)-2,2'-bipyrimidine (1) are used, more preferably about 1 eq to about 5 eq, and most preferably about 3 eq. In particularly preferred embodiments, the mono-protected ethylene glycol is reacted with the 4,6-dichloro-5-(2-methoxyphenoxy)-2,2'-bipyrimidine (1) in the presence of a base. Preferably the base is selected from the group comprising alkali metal hydroxides (such as lithium and sodium hydroxide), alkaline earth metal hydroxides, sodium metal, DBU, DBN, dimethylaminopyridine (DMAP), and pyridine. Most preferably the base is an alkali metal hydroxide and a particularly preferred base is sodium hydroxide. Preferably, the reaction is carried out in an organic solvent, which is preferably toluene but alternative solvents can be selected from the group comprising toluene, xylene, dimethyl sulfoxide (DMSO), tetrahydrofuran (THF), acetonitrile, dimethylformamide (DMF) and dimethylacetamide.

In step (b), compound (2a) is coupled with 4-tert-butyl phenyl sulfonamide. Preferably about 1 eq to about 2 eq of 4-tert-butyl phenyl sulfonamide relative to compound (2a) are used, preferably about 1 eq. Preferably the reaction is carried out in the presence of a base, such as potassium carbonate. A preferred reaction temperature is from about 100° C. to about 150° C., preferably about 120° C. A preferred reaction time is about 8-15 hours, preferably about 10 hours. Preferably the reaction is carried out in an organic solvent, such as DMSO.

In a further embodiment the ethylene glycol protecting moiety can be removed by any means known in the art. For example the inventors have found that acidification followed by treatment with a base is particularly efficient at removing the protecting group. Particularly preferred removal conditions involve treatment with formic acid followed by treatment with sodium hydroxide, particularly in the preferred embodiment wherein the protecting group is a tert-butyl ether moiety.

In another preferred embodiment the bosentan is isolated in step (d) by filtration and dried under reduced pressure until a constant weight is achieved.

The process according to the first aspect of the present invention is preferably carried out on an industrial scale, preferably providing bosentan in batches of about 500 g, 1 kg, 2 kg, 5 kg, 10 kg, 50 kg, 100 kg or more.

The process according to the first aspect of the present invention preferably provides bosentan in a molar yield of 30%, 40%, 50%, 60% or more from the dichloro compound of formula (1).

The process according to the first aspect of the present invention is preferably carried out without the use of chromatography.

The bosentan obtained by the process according to the first aspect of the present invention preferably has an HPLC purity of 97% or more, preferably 98% or more, preferably 99% or more, preferably 99.3% or more, preferably 99.5% or more, preferably 99.7% or more, preferably 99.8% or more, preferably 99.9% or more. Preferably the bosentan comprises less than about 0.1%, preferably less than about 0.05% of the dimer impurity (ii) (as measured by HPLC).

According to a second aspect of the invention, there is provided a novel compound of formula (2a) or salts or crystalline forms thereof:

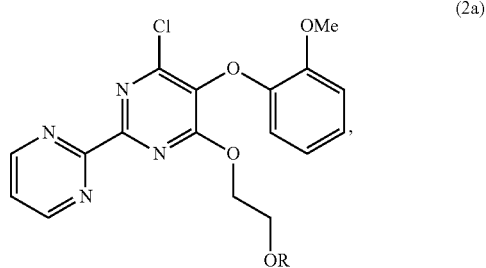

(2a)

wherein R is as previously described. Preferably R is tert-butyl, providing a compound having structure (2):

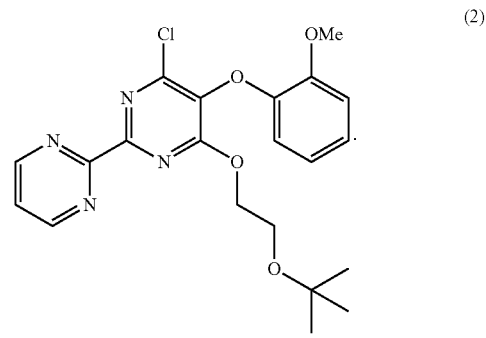 [SMILES: COc1ccccc1Oc1c(Cl)nc(-c2ncccn2)nc1OCCOC(C)(C)C]

(2)

It has been found that this compound is useful in the preparation of certain sulfonamide compounds, in particular bosentan. Of course it will be evident to the skilled person that different forms of the novel intermediate may be utilised in the working of the invention. They may comprise salt forms, different crystalline forms or amorphous forms, or isomers. The inventors have found that salts selected from the following group are particularly useful, said group comprising: a tartrate, succinate, oxalate, pimelate, adipate, acetate, suberate, salicylate, mesylate, malate, malonate, maleate, camphorsulfonate, mandelate, hydrochloride, hydrogen sulfate, sulfate, hydrobromide, besylate, benzoate, dihydrogen phosphate, glutarate, or citrate salt. Again it will be understood that the salts may be prepared by any means known in the art, in particular by reaction with the corresponding acid.

In a third aspect according to the invention there is provided a process for the preparation of a compound of formula (2a) comprising coupling a dichloro compound of formula (1) to a mono-protected ethylene glycol having formula $HOCH_2CH_2OR$, wherein R is as previously described. Preferably R is stable in basic and mildly acidic conditions, particularly preferred is wherein R may be selected from the group comprising alkyl, aryl, arylalkyl, allyl, silyl, benzoate and pivalate moieties, but most preferably R is tert-butyl. The skilled person will be aware that there are a number of further groups that may serve as protecting moieties on the ethylene glycol as previously described in relation to the first aspect of the present invention.

A preferred reaction temperature for this coupling is from about 15° C. to about 90° C., more preferably from about 30° C. to about 90° C., and most preferably from about 50° C. to about 60° C. A preferred reaction time is about 1-10 hours, more preferably about 1-5 hours, and most preferably about 1-3 hours. Preferably from about 1 equivalents (eq) to about 10 equivalents (eq) of mono-protected ethylene glycol relative to the dichloro compound of formula (1) are used, more preferably about 1 eq to about 5 eq, and most preferably about 3 eq. In particularly preferred embodiments, the mono-protected ethylene glycol is reacted with the 4,6-dichloro-5-(2-methoxyphenoxy)-2,2'-bipyrimidine (1) in the presence of a base. Preferably the base is selected from the group comprising alkali metal hydroxides (such as lithium and sodium hydroxide), alkaline earth metal hydroxides, sodium metal, DBU, DBN, DMAP, and pyridine. Most preferably the base is an alkali metal hydroxide and a particularly preferred base is sodium hydroxide. Preferably, the reaction is carried out in an organic solvent, which is preferably toluene but alternative solvents can be selected from the group comprising toluene, xylene, dimethyl sulfoxide (DMSO), tetrahydrofuran (THF), acetonitrile, dimethylformamide (DMF) and dimethylacetamide.

Preparing the mono-protected ethylene glycol pyrimidine derivative of formula (2a) or (2) using a mono-protected ethylene glycol derivative prevents formation of the undesired ethylene glycol bis-sulfonamide compound of formula (ii). Without being bound by any theory, it is believed that in some processes described in the prior art such as for example U.S. Pat. No. 5,292,740, the hydroxy group of some of the initially formed ethylene glycol derivative reacts with unreacted sodium ethylene glycol ($NaOCH_2CH_2OH$) or other bases which may be present in the reaction mixture to form an anion which then reacts with another molecule of pyrimidine mono-halide to produce the undesired ethylene glycol bis-sulfonamide derivative. By using the mono-protected ethylene glycol pyrimidine derivative (2a) or (2), the present invention eliminates any possibility of forming such an anion, thus completely eliminating production of the undesired ethylene glycol bis-sulfonamide derivative. This elimination of the production of the undesired ethylene glycol bis-sulfonamide derivative results in a higher overall product yield and easier product purification.

The process according to the third aspect of the present invention is preferably carried out on an industrial scale, preferably providing compound (2a) in batches of about 500 g, 1 kg, 2 kg, 5 kg, 10 kg, 50 kg, 100 kg or more.

The process according to the third aspect of the present invention preferably provides compound (2a) in a molar yield of 80%, 85%, 90% or more from the dichloro compound of formula (1).

The process according to the third aspect of the present invention is preferably carried out at a temperature of 90° C., 80° C., 70° C., 60° C. or less.

The process according to the third aspect of the present invention is preferably carried out without the use of chromatography.

In all of the aspects of the present invention described above, R is a hydroxyl protecting moiety. Preferably R is selected from the group comprising alkyl, alkenyl, alkynyl, aryl, arylalkyl, arylalkenyl, arylalkynyl, alkylaryl, alkenylaryl, alkynylaryl, allyl, silyl, benzoate and pivalate moieties. Preferably R is selected from the group comprising alkyl, aryl, arylalkyl, allyl, silyl, benzoate and pivalate moieties.

Alkyl, alkenyl and alkynyl moieties preferably comprise 1 to 12 carbon atoms, preferably 1 to 8 carbon atoms, preferably 1 to 6 carbon atoms, preferably 1 to 4 carbon atoms. A preferred alkyl moiety is tert-butyl.

Preferably an aryl moiety comprises 4 to 14 carbon atoms, preferably 6 to 10 carbon atoms. A typical aryl moiety is phenyl.

Arylalkyl, arylalkenyl, arylalkynyl, alkylaryl, alkenylaryl and alkynylaryl moieties preferably comprise 5 to 20 carbon atoms, preferably 7 to 15 carbon atoms. A typical arylalkyl moiety is benzyl.

Preferably an allyl moiety is a —$CH_2$—CH═CH—R' group, wherein R' is hydrogen or an alkyl, alkenyl, alkynyl, aryl, arylalkyl, arylalkenyl, arylalkynyl, alkylaryl, alkenylaryl or alkynylaryl group. Preferably R' is hydrogen.

Preferably a silyl moiety is a —$SiR'_3$ group, wherein R' is independently selected from hydrogen or an alkyl, alkenyl, alkynyl, aryl, arylalkyl, arylalkenyl, arylalkynyl, alkylaryl, alkenylaryl or alkynylaryl group. Typical silyl moieties are trimethylsilyl (TMS), triethylsilyl, triisopropylsilyl, dimethylisopropylsilyl, diethylisopropylsilyl, dimethyl-t-hexylsilyl, t-butyldimethylsilyl (TBDMS), t-butyldiphenylsilyl (TBDPS), tribenzylsilyl, tri-p-xylylsilyl, triphenylsilyl (TPS), diphenylmethylsilyl (DPMS), and t-butylmethoxyphenylsilyl (TBMPS).

In a further aspect there is provided a pharmaceutical composition comprising bosentan prepared by a process according to the invention. Preferably the composition is a solid composition, most preferably a tablet or capsule composition.

Illustrative of the invention is a pharmaceutical composition made by mixing bosentan according to the invention and a pharmaceutically acceptable carrier. In one embodiment of the invention there is provided a method for the treatment of an endothelin-receptor mediated disorder in a subject in need thereof, comprising administering to the subject a composition comprising a therapeutically effective amount of bosentan prepared according to the invention. In a further embodiment there is provided the use of bosentan prepared according to the invention substantially free of impurities, for the preparation of a medicament for treating an endothelin-receptor mediated disorder in a subject in need thereof, preferably the purity is greater than 97%, more preferably greater than 98%, more preferably still greater than 99%. In a particularly preferred embodiment a composition is provided for use in the treatment of circulatory and cardiovascular disorders. In a preferred embodiment the disorder is one or more of: hypertension, ischemia, pulmonary hypertension, vasospasm and angina pectoris. Endothelin-receptor mediated disorders comprise circulatory and cardiovascular disorders such as hypertension, ischemia, pulmonary hypertension, vasospasm and angina pectoris.

In addition to the active ingredient(s), the pharmaceutical compositions of the present invention may contain one or more excipients. Excipients are added to the composition for a variety of purposes. Diluents increase the bulk of a solid pharmaceutical composition and may make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. Carbopol®), carboxymethyl cellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminium silicate, maltodextrin, methyl cellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethyl cellulose calcium, carboxymethyl cellulose sodium (e.g. Ac-Di-Sol®, Prime-Hose®), colloidal silicon dioxide, croscarmellose sodium, crospovidone (e.g. Kollidon®, Polyplasdone®), guar gum, magnesium aluminium silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavouring agents and flavour enhancers make the dosage form more palatable to the patient. Common flavouring agents and flavour enhancers for pharmaceutical products that may be included in the composition of the present invention include maltol, vanillin, ethyl vanillin, menthol, citric acid, fumaric acid, ethyl maltol and tartaric acid.

Solid compositions may also be dyed using any pharmaceutically acceptable colourant to improve their appearance and/or facilitate patient identification of the product and unit dosage level.

The solid compositions of the present invention include powders, granulates, aggregates and compacted compositions.

The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts. For solid oral dosage forms amounts of active ingredient between the ranges of about 10-200 mg per unit dose are preferred, particularly preferred is an amount between about 50-130 mg per unit dose.

Preferably the composition is a solid composition, most preferably a tablet or capsule composition.

The dosage form of the present invention may be a capsule containing the composition, preferably a powdered or granulated solid composition of the invention, within either a hard or a soft shell. The shell may be made from gelatin and optionally contain a plasticizer such as glycerine and sorbitol, and an opacifying agent or colourant.

The active ingredient and excipients may be formulated into compositions and dosage forms according to methods known in the art.

A composition for tableting or capsule filling may be prepared by wet granulation. In wet granulation, some or all of the active ingredient and excipients in powder form are blended and then further mixed in the presence of a liquid, typically water, that causes the powder to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry granulation. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

In further embodiments the composition of the invention may further comprise one or more additional active ingredients.

In a further aspect, the composition according to the invention is provided for use in the treatment of disorders which are associated with endothelin activities.

The details of the invention, its objects and advantages are explained hereunder in greater detail in relation to non-limiting exemplary illustrations.

EXAMPLES

Preparation of Bosentan

A process according to the invention is represented below as a schematic diagram. The compound number descriptors refer to the numbered compounds in the schematic diagram.

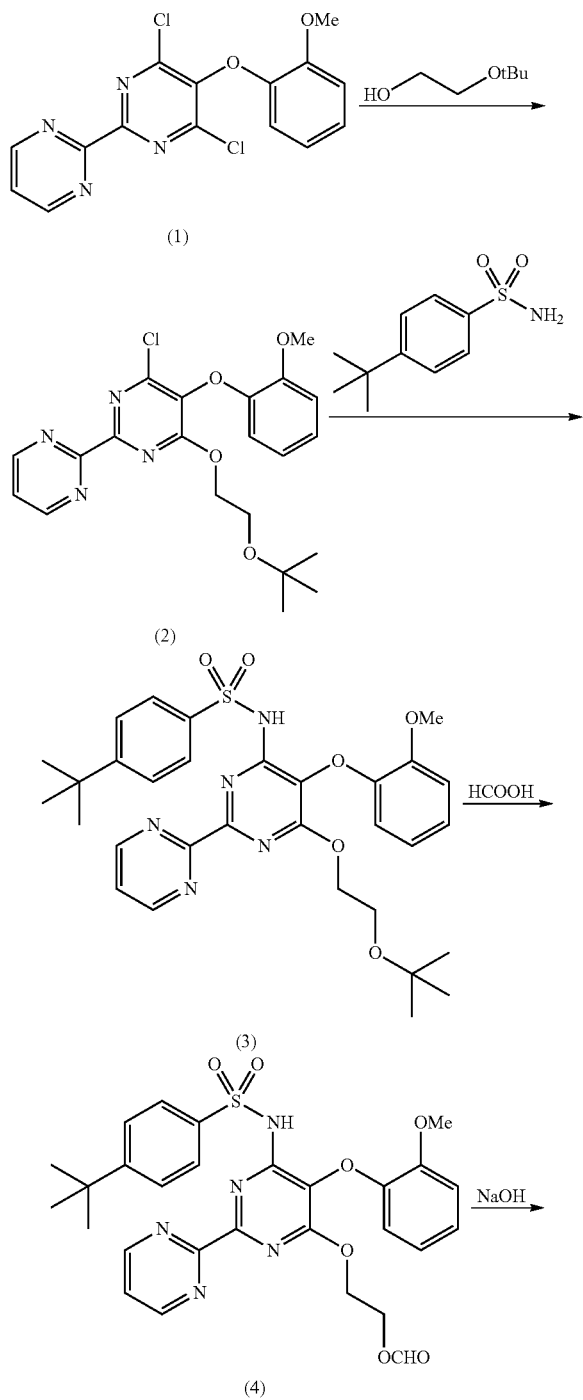

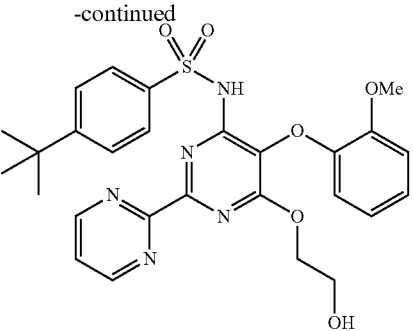

bosentan (i)

Process for Conversion of Compound (1) to (2) (Stage 1)

Sodium hydroxide (1 eq) was added to ethylene glycol mono tert-butyl ether (3 eq) in toluene (7 vol). Compound (1) (1 eq) was added and the reaction mixture heated at 55° C. for 2 hours. After completion of the reaction, the mixture was acidified with a 1:1 mixture of concentrated HCl and water (0.4 vol) to pH 2. The organic layer was separated and washed with water (5 vol). The toluene was distilled off at 40° C. under vacuum (10 mbar) and the product (compound (2)) was obtained as a light brown solid (molar yield=90%).

Process for Conversion of Compound (2) to (3) (Stage 2)

A mixture of DMSO (10 vol), potassium carbonate (1.2 eq), 4-tert-butyl phenyl sulfonamide (1 eq) and compound (2) (1 eq) was heated at 120° C. for 10 hours. After completion of the reaction, water (25 vol) was added to the reaction mixture, the reaction mixture was acidified with a solution of tartaric acid (1.8 eq) in water (25 vol) to pH 3, and the precipitated solid was filtered under vacuum and dried under vacuum (10 mbar) at 50° C. for 2 hours. The product (compound (3)) was obtained as a light brown solid (molar yield=100%).

Process for Conversion of Compound (3) to (4) (Stage 3)

Compound (3) (1 eq) in formic acid (2 vol) was heated at 85° C. for 4 hours. Toluene (8.3 vol) was added to the reaction mixture and the formic acid distilled out azeotropically using toluene under vacuum (10 mbar) at 50° C. The brown thick oil obtained was taken in ethanol (3.3 vol) and heated to reflux. The clear solution was cooled to 25-30° C., stirred for 3 hours and the resultant solid filtered. The wet solid was mixed with ethanol (1.6 vol), heated to reflux and cooled to 25-30° C. The resultant solid (compound (4)) was then filtered (molar yield=47%).

Process for Conversion of Compound (4) to Bosentan (i) (Stage 4)

Compound (4) (1 eq) was taken in ethanol (2.5 vol) and added to a solution of sodium hydroxide (3 eq) in water (2 vol). Water (6 vol) was added to the clear solution and stirred at 25-30° C. for 1 hour. The reaction mixture was acidified with concentrated HCl (0.33 vol) to pH 5.5, water (10 vol) was added, and the mixture stirred for 1 hour and filtered. A white solid was obtained which was dried under vacuum for 4 hours. The resultant bosentan had a HPLC purity=99.71% (molar yield=93%).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A process for preparing bosentan comprising:
   (a) reacting a dichloro compound of formula (1) with a mono-protected ethylene glycol of formula HOCH₂CH₂OR, wherein R is a hydroxyl protecting moiety, to afford a compound of formula (2a):

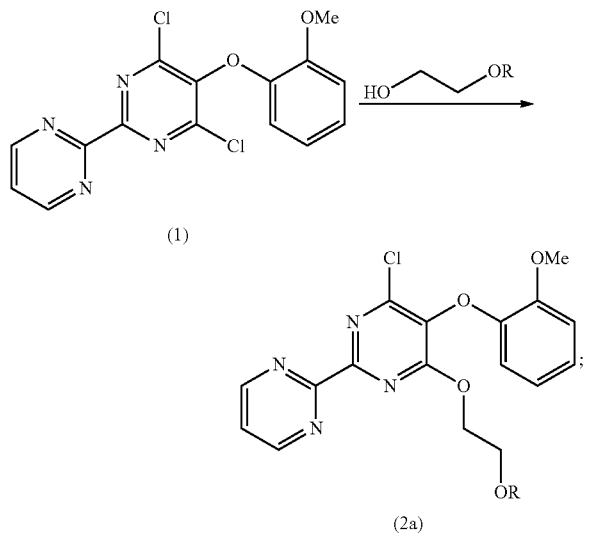

(b) coupling compound (2a) with 4-tert-butyl phenyl sulfonamide;
   (c) removing the protecting moiety R; and
   (d) isolating bosentan from the mixture obtained in step (c).

2. A process according to claim 1, wherein R is selected from the group consisting of alkyl, aryl, arylalkyl, allyl, silyl, benzoate, pivalate and t-butyl.

3. A process according to claim 1, wherein in step (a) the dichloro compound of formula (1) and the mono-protected ethylene glycol are reacted in the presence of a base selected from the group consisting of sodium metal, DBU, DBN, DMAP, pyridine, lithium hydroxide and sodium hydroxide.

4. A process according to claim 1, wherein step (a) is carried out in an organic solvent selected from the group consisting of toluene, THF, xylene, DMF, DMSO, acetonitrile and dimethylacetamide.

5. A compound having the structure as shown in formula (2a) or a salt or crystalline form thereof:

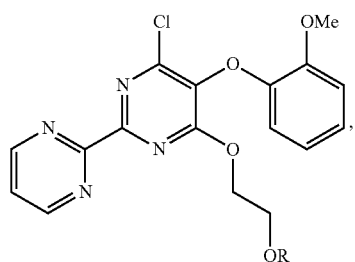

wherein R is a hydroxyl protecting moiety.

6. A compound according to claim 5, wherein R is selected from the group consisting of alkyl, aryl, arylalkyl, allyl, silyl, benzoate, pivalate and tert-butyl.

7. A compound according to claim 5, wherein the salt is selected from the group consisting of a tartrate, succinate, oxalate, pimelate, adipate, acetate, suberate, salicylate, mesylate, malate, malonate, maleate, camphorsulfonate, mandelate, hydrochloride, hydrogen sulfate, sulfate, hydrobromide, besylate, benzoate, dihydrogen phosphate, glutarate, and citrate salt.

8. A process for preparing a compound of formula (2a) comprising coupling a dichloro compound of formula (1) to a mono-protected ethylene glycol of formula HOCH₂CH₂OR, wherein R is a hydroxyl protecting moiety, to afford a compound of formula (2a):

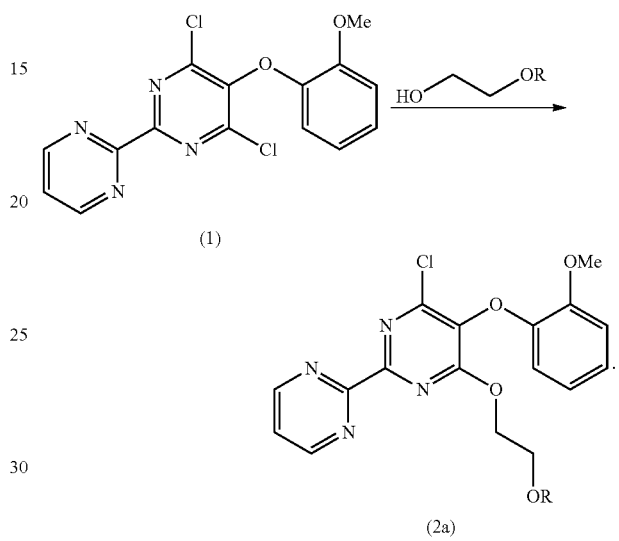

9. A process according to claim 8, wherein R is selected from the group consisting of alkyl, aryl, arylalkyl, allyl, silyl, benzoate, pivalate and tert-butyl.

10. A process according to claim 8, wherein the dichloro compound of formula (1) is coupled to the mono-protected ethylene glycol in the presence of a base selected from the group consisting of sodium metal, DBU, DBN, DMAP, pyridine, lithium hydroxide and sodium hydroxide.

11. A process according to claim 8, wherein the reaction mixture is heated to between about 30-90° C.

12. The process according to claim 1, wherein in step (a) the dichloro compound of formula (1) and the mono-protected ethylene glycol are reacted in the presence of a base selected from the group consisting of alkali metal hydroxides and alkaline earth metal hydroxides.

13. The process according to claim 1, wherein the reaction mixture in step (a) is heated to between about 30-90° C.

14. The process according to claim 13, wherein the reaction mixture in step (a) is heated to between about 50-60° C.

15. The process according to claim 1, wherein the bosentan is isolated in step (d) by filtration and then dried under reduced pressure until a constant weight is achieved.

16. The process according to claim 8, wherein the dichloro compound of formula (1) is coupled to the mono-protected ethylene glycol in the presence of a base selected from the group consisting of alkali metal hydroxides and alkaline earth metal hydroxides.

17. The process according to claim 8, wherein the dichloro compound of formula (1) is coupled to the mono-protected ethylene glycol in the presence of an organic solvent selected from the group consisting of toluene, THF, xylene, DMF, DMSO, acetonitrile, and dimethylacetamide.

18. The process according to claim 11, wherein the reaction mixture is heated to between about 50-60° C.

* * * * *